United States Patent [19]

Bjornson et al.

[11] Patent Number: 5,086,030

[45] Date of Patent: Feb. 4, 1992

[54] GAMMA-BUTYROLACTONE PRODUCTION CATALYST

[75] Inventors: Geir Bjornson; Joel J. Stark, both of Bartlesville, Okla.

[73] Assignee: Phillips Petroleum Company, Bartlesville, Okla.

[21] Appl. No.: 566,987

[22] Filed: Aug. 14, 1990

Related U.S. Application Data

[62] Division of Ser. No. 389,350, Aug. 3, 1989, Pat. No. 4,968,818.

[51] Int. Cl.$^5$ .................. B01J 21/08; B01J 23/36; B01J 23/84
[52] U.S. Cl. .................................. 502/241; 502/259
[58] Field of Search ..................... 502/241, 259

[56] References Cited

U.S. PATENT DOCUMENTS

| | | |
|---|---|---|
| 3,492,314 | 1/1970 | Asano et al. ................. 502/326 |
| 3,758,512 | 9/1973 | Kanetaka et al. .............. 502/259 |
| 3,890,361 | 6/1975 | Kanetaka et al. .............. 260/343.6 |
| 3,994,928 | 11/1976 | Michalczyk et al. ............ 502/260 |
| 4,001,282 | 1/1977 | Miller ........................ 260/343.6 |
| 4,006,165 | 2/1977 | Michalczyk et al. ............ 260/343.6 |
| 4,025,534 | 5/1977 | Sandhack et al. .............. 260/343.6 |
| 4,048,196 | 9/1977 | Broecker et al. .............. 260/346.11 |
| 4,052,335 | 10/1977 | Michalyczyk et al. ........... 252/446 |
| 4,083,809 | 4/1978 | De Thomas et al. ............. 252/457 |
| 4,096,156 | 6/1978 | Freudenberger et al. ......... 260/343.6 |
| 4,105,674 | 8/1978 | De Thomas et al. ............. 260/343.6 |
| 4,668,654 | 5/1987 | Drake ......................... 502/259 |

FOREIGN PATENT DOCUMENTS

| | | | |
|---|---|---|---|
| 251550 | 11/1987 | Fed. Rep. of Germany ...... | 502/259 |
| 2078745 | 1/1982 | United Kingdom ............ | 502/241 |

*Primary Examiner*—Carl F. Dees
*Attorney, Agent, or Firm*—Laney, Dougherty, Hessin & Beavers

[57] ABSTRACT

A catalytic hydrogenation process for converting maleic anhydride and/or succinic anhydride to gamma-butyrolactone, a novel selective catalyst for use in such process and a method of preparing the catalyst are provided. The process comprises contacting maleic anhydride and/or succinic anhydride with hydrogen in the presence of catalysts whereby the anhydride is converted to predominantly gamma-butyrolactone. The catalyst of the invention is comprised of transition metals, their oxides and mixtures thereof on a silica gel support having a high surface area and pore volume.

12 Claims, No Drawings

GAMMA-BUTYROLACTONE PRODUCTION CATALYST

This is a continuation of copending application Ser. No. 07/389,350 filed on 8/3/89 U.S. Pat. No. 4,968,818.

BACKGROUND OF THE INVENTION

1. Field of the Invention

The present invention relates generally to a gamma-butyrolactone production process and catalyst, and more particularly, to a process and catalyst for producing gamma-butyrolactone from maleic anhydride and/or succinic anhydride.

2. Description of the Prior Art 10 Gamma-butyrolactone is a stable compound which has a variety of uses, not the least of which is as an intermediate in the manufacture of various other compounds, e.g., vinylpyrrolidone.

The exothermic catalytic hydrogenation of maleic anhydride or succinic anhydride and/or other related compounds to produce gamma-butyrolactone is old and well established in the art. For example, U.S. Pat. No. 4,025,534 issued May 24, 1977 discloses a continuous process for producing gamma-butyrolactone by hydrogenating maleic anhydride in the presence of a catalyst comprised of cobalt oxide and palladium on a support of silica. The hydrogenation is carried out in two stages, the first at a temperature of 52° C. to 100° C. and the second at a temperature of 190° C. to 220° C.

U.S. Pat. No. 3,492,314 issued Jan. 27, 1970 is directed to a process for producing tetrahydrofuran and gamma-butyrolactone from maleic anhydride in a two-stage catalytic hydrogenation reaction or from succinic anhydride in a single stage catalytic hydrogenation reaction. The catalyst utilized in both processes is a nickel-rhenium catalyst supported on a carrier, such as silica gel, alumina, silica-alumina and the like.

While the prior art processes and catalysts have been utilized successfully in the production of gamma-butyrolactone, various reaction products in addition to gamma-butyrolactone are usually produced in significant quantities, often making the processes less than economically optimum. Examples of such additional reaction products are n-butynol, n-propanol, n-butyric acid, propionic acid, succinic acid and tetrahydrofuran. The processes and catalysts of the present invention, on the other hand, bring about high gamma-butyrolactone selectivity and high quantitative conversion of maleic anhydride and/or succinic anhydride to gamma-butyrolactone.

Thus, by the present invention an improved process for the production of gamma-butyrolactone from maleic anhydride and/or succinic anhydride starting materials are provided as well as a novel highly selective catalyst and a method of preparing such catalyst.

SUMMARY OF THE INVENTION

An improved process for converting maleic anhydride and/or succinic anhydride to gamma-butyrolactone which comprises contacting the anhydride with hydrogen in the presence of a novel selective catalyst is provided. The catalyst is comprised of transition metals, their oxides and mixtures thereof selected from the group consisting of nickel, cobalt, nickel oxide, cobalt oxide, cobalt rhenium oxide and nickel rhenium oxide supported on silica gel having a very high surface area and pore volume, i.e., a surface area in the range of from about 50 to about 500 $m^2/g$ and a pore volume in the range of from about 0.25 cc/g to about 2.0 cc/g.

An improved two-stage process for converting maleic anhydride to gamma-butyrolactone is also provided which comprises reacting the maleic anhydride with hydrogen in a first stage in the presence of a first catalyst to produce a predominantly succinic anhydride reaction product, and then reacting the succinic anhydride reaction product from the first stage with hydrogen in a second stage in the presence of the novel selective catalyst described above to produce a predominantly gamma-butyrolactone reaction product therefrom. The first stage catalyst is preferably comprised of transition metals, their oxides and mixtures thereof selected from the group consisting of cobalt, cobalt oxide palladium, nickel, nickel oxide, rheniuum and rhenium oxides supported on silica gel having a relatively low surface area and pore volume, i.e., a surface area in the range of from about 0.5 to about 100 $m^2/g$ and a pore volume in the range of from about 0.1 cc/g to about 1.0 cc/g.

The novel highly selective catalyst of this invention for the exothermic catalytic hydrogenation of succinic anhydride to gamma-butyrolactone provides high selectivity and conversion of the succinic anhydride to gamma-butyrolactone. The transition metals, their oxides and mixtures thereof utilized in the catalyst are deposited on the supporting silica gel in relatively low amounts to prevent exothermic run-away, and the metal forms are uniformly distributed over the silica gel.

It is, therefore, a general object of the present invention to provide a gamma-butyrolactone production process and catalyst therefor.

A further object of the present invention is the provision of an improved process for converting maleic anhydride and/or succinic anhydride to gamma-butyrolactone utilizing a novel highly selective catalyst.

Another object of the present invention is the provision of a highly selective catalyst for converting succinic anhydride to gamma-butyrolactone and a method of preparing such catalyst.

Other and further objects, features and advantages of the present invention will be readily apparent to those skilled in the art upon a reading of the description of preferred embodiments which follows.

DESCRIPTION OF PREFERRED EMBODIMENTS

This invention relates in one aspect to a single stage process for catalytically hydrogenating succinic anhydride to gamma-butyrolactone using a novel highly selective transition metal and metal oxide catalyst. In another aspect, a two-stage process is provided for converting maleic anhydride to gamma-butyrolactone. That is, in a first stage, the maleic anhydride is catalytically hydrogenated to a succinic anhydride reaction product utilizing a conventional transition metal and metal oxide catalyst. The succinic anhydride reaction product is then catalytically hydrogenated to a gamma-butyrolactone reaction product utilizing the aforementioned novel catalyst of high selectivity and conversion.

The novel catalyst of the present invention utilizes selected transition metals, their oxides and mixtures thereof on a high surface area and high pore volume silica gel support in relatively low concentrations. More specifically, the catalyst is comprised of transition metals, their oxides and mixtures thereof supported on silica gel having a surface area in the range of from about 50 to about 500 m²/g and a pore volume in the range of from about 0.25 cc/g to about 2.5 cc/g. Such silica gel has an average pore diameter of from about 25 angstroms to about 200 angstroms. A 25 particularly preferred such silica gel has a surface area of about 310 m²/g, a pore volume of about 1.3 cc/g and a density of about 0.77 grams/cc and is marketed by the Davison Company under the trade designation G-57 Silica Gel.

Various transition metals, their oxides and mixtures of the metals and oxides can be utilized in the catalyst, i.e., nickel, cobalt, nickel oxide, cobalt oxide, cobalt rhenium oxide (cobalt rehenate) and nickel rhenium oxide (nickel rehenate).

The transition metals, their oxides and mixtures thereof are preferably present on the above-described silica gel in an amount in the range of from about 0.1% by weight to about 10.0% by weight of the catalyst including the silica gel. A preferred specific such catalyst is comprised of nickel present in an amount of about 4% by weight and nickel oxide present in an amount of about 2.5% by weight with the remainder being silica gel. Another preferred such catalyst is comprised of cobalt rhenium oxide supported on the silica gel wherein the cobalt rhenium oxide is present in an amount in the range of from about 0.5% by weight to about 5.0% by weight of the catalyst, most preferably about 2.5% by weight of the catalyst. Yet another preferred such catalyst is comprised of nickel rhenium oxide present in an amount in the range of from about 0.5% by weight to about 5.0% by weight of the catalyst, most preferably about 2.5% by weight of the catalyst. As stated above, the catalysts of this invention are particularly useful in the exothermic catalytic hydrogenation of succinic acid to gamma-butyrolactone and produce high selectivity and conversion in such reaction.

As stated above, the catalyst of this invention is prepared utilizing a silica gel support having a surface area in the range of from about 50 to about 500 m²/g and a pore volume in the range of from about 0.25 cc/g to about 2.5 cc/g, most preferably a surface area of 130 m²/g and a pore volume of about 1.3 cc/g. The silica gel is first calcined at a temperature and for a time period sufficient to remove reactive hydroxyl groups therefrom. Generally, the calcining step is carried out in atmospheric air at a temperature in the range of from about 300° C. to about 550° C. for a time period in the range of from about 3 hours to about 24 hours. Most preferably, the silica gel is calcined at a temperature of about 535° C. for a time period of about 3 hours.

Following the calcining step, the silica gel is impregnated with an alcohol solution of transition metal salts which are thermally decomposable to the transition metals, their oxides and mixtures thereof desired. The alcohol is preferably methanol, and the transition metal salts can be, for example, nitrates, formates, acetates, or other decomposable organic anion. The quantity of transition metal salts in the alcohol solution utilized and the quantity of alcohol solution containing the salts used for impregnating the calcined silica gel are controlled whereby upon decomposition, the resulting metals and oxides formed are present on the catalyst in a total amount less than about 10% by weight of the catalyst. Because of the high surface area of the silica gel, the transition metal salts are uniformly distributed on the silica gel. Further, because of the high porosity of the silica gel, the transition metal salts and resulting forms thereof after decomposition are held as liquids on the silica gel. This allows the efficient transfer of heat into and out of the catalyst particles.

After the impregnation step has been completed, the methanol on the silica gel is allowed to evaporate very slowly at room temperature, i.e., over a time period for 24 hours or more. The resulting impregnated silica gel is then heated in an inert gas atmosphere, e.g., nitrogen, at a temperature and for a time period sufficient to decompose the transition metal salts to the desired transition metals, their oxides or mixtures thereof. This step is preferably carried out using an incremental temperature increasing procedure whereby the temperature is elevated to about 550° C. over a 5 hour time period. More specifically, the catalyst is preferably heated to a temperature of about 130° C. and held at such temperature for a time period of about 60 minutes, heated to a temperature of 260° C. and held at such temperature for a time period of about 60 minutes, heated to a temperature of 390° C. and held at such temperature for about 60 minutes, heated to a temperature of 520° C. and held at such temperature for about 60 minutes, and then heated to a final temperature of 550° C. and held at such temperature for a time period of about 60 minutes. Finally, the catalyst is activated by heating it in a hydrogen atmosphere in the reaction reactor at a temperature in the range of from about 75° C. to about 300° C. for a time period in the range of from about 12 hours to about 24 hours.

The reaction of maleic anhydride with hydrogen in the presence of a catalyst is exothermic and produces succinic anhydride. The succinic anhydride in turn is exothermically converted to gamma-butyrolactone when hydrogenated in the presence of a catalyst. These reactions can be represented as follows:

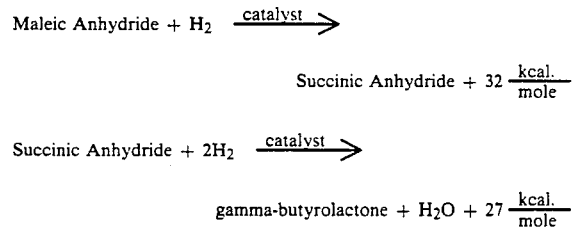

Maleic Anhydride + $H_2$ $\xrightarrow{\text{catalyst}}$ Succinic Anhydride + $32 \frac{\text{kcal.}}{\text{mole}}$ Succinic Anhydride + $2H_2$ $\xrightarrow{\text{catalyst}}$ gamma-butyrolactone + $H_2O$ + $27 \frac{\text{kcal.}}{\text{mole}}$ In carrying out the process of the present invention for converting succinic anhydride to gamma-butyrolactone, the succinic anhydride is contacted with hydrogen in the presence of the novel selective catalyst described above, i.e., a catalyst comprised of transition metals, their oxides and mixtures thereof selected from the group consisting of nickel, cobalt, nickel oxide, cobalt oxide, cobalt rhenium oxide and nickel rhenium oxide supported on silica gel having a surface area in the range of from about 50 m²/g to about 500 m²/g and a pore volume in the range of from about 0.25 cc/g to about 2.5 cc/g.

Of the various transition metals, oxides and mixtures which can be used, catalysts containing a mixture of nickel and nickel oxide, a single cobalt rhenium oxide component or a single nickel rhenium oxide component in amounts below about 10% by weight of the catalyst are preferred. The most preferred nickel-nickel oxide catalyst contains about 6% by weight nickel, which is comprised of nickel in an amount of about 4% by weight of the catalyst and nickel oxide in an amount of about 2.5% by weight of the catalyst supported on the above-described high surface area and high pore volume silica gel. When cobalt rhenium oxide or nickel rhenium oxide catalysts are used, the cobalt rhenium or nickel rhenium are each most preferably present in the catalyst in an amount of about 2.5% by weight of the catalyst.

The process is preferably carried out at a temperature in the range of from about 200° C. to about 240° C. and at a pressure in the range of from about 900 psig to about 1500 psig. The succinic anhydride can be reacted in the molten state or, more preferably, in a solvent such as tetrahydrofuran. The weight hourly space velocity of the succinic anhydride with respect to the catalyst is preferably in the range of from about 0.3 to about 2.0 grams of succinic anhydride per gram of catalyst per hour.

The process is advantageously carried out using a trickle-column reactor containing the catalyst used. In order to prevent exothermic runaway and control the reaction temperature at a substantially constant level within the above described range, the catalyst can be graded with a diluent, such as carborundum, whereby a relatively low concentration of catalyst is present at the top of the reactor increasing to a high concentration at the bottom of the reactor. The trickle-column reactor preferably also includes additional means for controlling the temperature of the reaction carried out therewithin by the removal of heat from the reactor. A preferred trickle-column reactor arrangement including heat removal means is comprised of a trickle-column reactor surrounded by a heat exchange section through which a cooling medium such as oil or steam is circulated. Heat is transferred through the reactor walls to the cooling medium and the cooling medium is circulated at a rate whereby the temperature within the reactor is controlled at a substantially constant desired level.

A continuous stream of succinic anhydride in an 80% by weight tetrahydrofuran solution is preferably introduced to the top of the trickle-column reactor. As the solution flows downwardly over the catalyst contained in the reactor, it is contacted with hydrogen at a mole ratio of hydrogen to succinic anhydride in the range of from about 1.3 to about 5.0. A recycle stream of succinic acid and/or succinic anhydride with some gamma-butyrolactone therein is preferably also introduced at the top of the reactor. Succinic acid becomes more soluble when gamma-butyrolactone is part of the stream. The recycle stream increases the conversion of succinic anhydride to gamma-butyrolactone and is utilized at a flow rate of at least 15% of the flow rate of the feed solution The process has a high selectivity to gamma-butyrolactone, i.e., a selectivity generally in the range of from about 92% to about 96%, and a high conversion, i.e., a conversion in the range of from about 20% to about 90% by weight of succinic anhydride feed.

The two-stage process of the present invention for producing gamma-butyrolactone from maleic anhydride comprises reacting the maleic anhydride with hydrogen in a first stage in the presence of a first selective catalyst to produce a predominantly succinic anhydride reaction product. The first stage catalyst can be any of various conventional catalysts heretofore utilized for converting maleic anhydride to succinic anhydride. Preferably, the first stage catalyst is comprised of transition metals, their oxides and mixtures thereof selected from the group consisting of cobalt, cobalt oxide, palladium, nickel, nickel oxide, rhenium and rhenium oxides supported on silica gel having a surface area in the range of from about 0.5 m$^2$/g to about 100 m$^2$/g and a pore volume in the range of from about 0.1 cc/g to about 1.0 cc./g. The transition metals, oxides and mixtures utilized are preferably present in the catalyst in an amount in the range of from about 1% to about 50% by weight of the catalyst. The most preferred first stage catalyst is comprised of cobalt oxide present in an amount of about 25% by weight of the catalyst and palladium present in an amount of about 0.6% by weight of the catalyst supported on silica gel having a surface area of about 34 m$^2$/g and a pore volume of about 0.18 cc/g.

The predominantly succinic anhydride reaction product from the first stage reaction is reacted with hydrogen in a second stage in the presence of the novel selective catalyst of the present invention described above to produce a predominantly gamma-butyrolactone reaction product therefrom. The second stage reaction catalyst most preferably contains 6% by weight nickel, which is comprised of nickel present in an amount of about 4% by weight of the catalyst and nickel oxide present in an amount of about 2.5% by weight of the catalyst supported on silica gel having a surface area in the range of from about 100 to about 500 m$^2$/g and a pore volume in the range of from about 0.2% to about 2.0%.

The first stage reaction is preferably carried out in a first trickle-column reactor containing the first stage catalyst graded by a diluent such as carborundum. The second stage reaction is preferably carried out in a separate second trickle-column reactor containing the second stage catalyst also graded with carborundum. The mole ratio of hydrogen to maleic anhydride in the first stage is preferably in the range of from about 1.3 to about 2.0, most preferably about 1.5. More hydrogen is added between the reactors so the mole ratio of hydrogen to succinic anhydride in the second stage is preferably from about 1.4 to 5.0, most preferably about 2.3.

Both trickle-column reactors preferably include heat removal means of the type described above for controlling the temperature of the reactions carried out therewithin at substantially constant levels.

The maleic anhydride feed containing about 40% to 50% by weight maleic anhydride and about 50% to 60% by weight tetrahydrofuran is continuously introduced to the first stage trickle-column reactor, preferably at a weight hourly space velocity in the range of from about 0.3 to about 2.0 grams of maleic anhydride per gram of catalyst per hour. A recycle stream containing gamma-butyrolactone: can optionally be added at the top of the first stage reactor to aid in solubilizing the formed succinic acid and succinic anhydride. The first stage reaction is preferably carried out at a substantially constant temperature within the range of from about 105° C. to about 130° C., most preferably at a temperature of about 120° C.; and the second stage reaction is preferably carried out at a substantially constant temperature within the range of from about 200° C. to about 240° C., most preferably at a temperature of about 220° C. The pressure at which the reactions in both stages are carried out is preferably in the range of from about 900 psig to about 1500 psig. The weight hourly space velocity of the succinic anhydride reaction mixture in the second stage is preferably in the range of from about 0.4 to about 2.0 grams of maleic anhydride per gram of catalyst per hour. The two-stage process has a high selectivity to gamma-butyrolactone, i.e., a selectivity in the range of from about 86% to about 94%, and a conversion in the range of from about 40% to about 80% by weight of maleic anhydride feed.

In a particularly preferred technique for carrying out the process of the present invention, the first and second trickle-column reactors are cooling medium jacketed, and the jackets each contain a reservoir of water which converts to steam. The reaction temperatures in the reactors are controlled by relieving steam from the jackets at pressures corresponding to the desired temperatures, e.g., 120° C. in the first reactor and 220° C. in the second reactor. A recycle stream containing gamma-butyrolactone to increase the solubility of the succinic anhydride in the first stage reaction mixture is utilized in the first stage reactor. Additional hydrogen and a recycle stream of succinic acid and/or succinic anhydride containing some gamma-butyrolactone are added at the top of the second stage reactor. The recycle stream increases the concentration of succinic anhydride and its conversion to gamma-buryrolactone.

In order to more fully illustrate the present invention and to facilitate a clear understanding thereof, the following examples are given.

EXAMPLE 1

Nickel-cobalt catalysts of the present invention were each prepared by first calcining silica gel (Davison G-57) in air at 535° C. for 3 hours. The calcined silica gel was then impregnated with a methanol solution of nickel acetate and cobalt acetate. The methanol was evaporated from the silica gel in air for 24 hours, and then heated in the presence of nitrogen at increasing temperature levels over about 7 hours, i.e., at 130° C. for 60 min.; at 260° C. for 60 min.; at 390° C. for 60 min.; at 520° C. for 60 min.; and at 550° C. for 60 min. Finally, the catalyst was activated by heating in the presence of hydrogen at 310° C. for about 24 hours in a steam jacketed trickle bed reactor.

Catalysts prepared as above comprised of (expressed in weight % of the catalyst) 1.2% nickel and 2.4% cobalt; 4.8% nickel and 2.4% cobalt; 1.16% nickel and 2.32% cobalt; and 5.65% nickel were tested for effectiveness in the hydrogenation of succinic anhydride to gamma-butyrolactone. The tests were carried out by introducing a 15% by weight solution of succinic anhydride in tetrahydrofuran into the top of a trickle-column reactor (76 cms. long × 2.6 cms. in diameter) filled with the catalyst tested in particles having sizes of 10 to 30 mesh. Hydrogen was injected at the top of the column and the selectivity to gamma-butyrolactone as well as the rate of conversion of succinic anhydride to gamma-butyrolactone were determined. The results of the tests are given in Table I below.

TABLE I

Effectiveness of Nickel and Cobalt Catalysts

| Run No. | Catalyst Wt. % Ni | Wt. % Co | Feed (Wt. %) Succinic Anhydride in Tetra-hydro-furan | Temperature (°C.) | Pressure (psig) | Weight Hourly Space Velocity (gms. of succinic anhydride per gm. of catalyst per hour) | Hydrogen Flow (mole ratio of hydrogen to succinic anhydride) | Selectivity (Wt. % of gamma-butyrolactone in reaction product) | Conversion (Wt. %) of succinic anhydride to gamma-butyrolactone |
|---|---|---|---|---|---|---|---|---|---|
| 1 | 1.2 | 2.4 | 15 | 210 | 900 | 0.505 | 1.33 | 96.7 | 42.0 |
| 2 | 1.2 | 2.4 | 15 | 223 | 900 | 0.488 | 1.38 | 97.9 | 69.0 |
| 3 | 1.2 | 2.4 | 15 | 232 | 1200 | 0.465 | 1.42 | 98.0 | 42.0 |
| 4 | 1.2 | 2.4 | 15 | 234 | 1200 | 0.465 | 1.42 | 96.0 | 47.0 |
| 5 | 1.2 | 2.4 | 15 | 234 | 1200 | 0.460 | 1.45 | 98.0 | 49.0 |
| 6 | 1.2 | 2.4 | 15 | 234 | 1200 | 0.460 | 1.45 | 97.0 | 48.0 |
| 7 | 1.2 | 2.4 | 15 | 229 | 1500 | 0.130 | 3.06 | 74.5 | 100.0 |
| 8 | 1.2 | 2.4 | 15 | 231 | 1500 | 0.200 | 2.04 | 97.3 | 72.3 |
| 9 | 4.8 | 4.8 | 15 | 220 | 900 | 0.368 | 1.52 | 94.5 | 83.7 |
| 10 | 2.4 | 2.4 | 15 | 211 | 1500 | 0.366 | 2.19 | 97.1 | 79.0 |
| 11 | 1.16 | 2.4 | 15 | 230 | 600 | 0.350 | 4.61 | 93.8 | 86.6 |
| 12 | 1.16 | 2.4 | 15 | 230 | 900 | 0.350 | 4.53 | 97.0 | 82.5 |
| 13 | 1.16 | 2.4 | 15 | 230 | 900 | 0.290 | 5.40 | 95.6 | 69.3 |
| 14 | 1.16 | 2.4 | 15 | 230 | 900 | 0.290 | 5.40 | 96.5 | 75.4 |
| 15 | 5.65 | 0 | 15 | 209 | 900 | 0.890 | 2.21 | 95.1 | 78.5 |
| 16 | 5.65 | 0 | 15 | 210 | 900 | 0.890 | 2.21 | 96.7 | 76.5 |
| 17 | 5.65 | 0 | 15 | 216 | 900 | 0.930 | 2.24 | 89.6 | 83.2 |
| 18 | 5.65 | 0 | 15 | 216 | 900 | 0.930 | 2.24 | 91.0 | 93.2 |

From Table I it can be seen that both the nickel-cobalt catalysts and nickel-only catalysts gave better than 95 wt.% selectivities at conversions below about 80 wt.%. The nickel-only form of the catalyst was effective at high succinic anhydride throughputs at lower hydrogen mole ratios.

EXAMPLE 2

Various additional catalysts were prepared in accordance with the procedure of Example 1 as follows: 6.65% nickel and 1.65% cobalt; 8.27% cobalt; 5.65% nickel; 4.8% nickel and 1.2% cobalt; and 5.58% nickel and 1.4% cobalt. The catalysts were tested for effectiveness in accordance with the procedure of Example 1 except that additional components representing recycle streams were added to the feeds. The results of these tests are given in Table II below.

TABLE II

Effectiveness of Nickel and Cobalt Catalysts with Various Recycle Components

| Run No. | Catalyst Wt. % Ni | Catalyst Wt. % Co | Feed Wt. % Succinic Anhydride | Feed Wt. % Tetrahydrofuran | Feed Wt. % Gamma-Butyrolactone | Feed Wt. % Succinic Acid | Temperature (°C.) | Pressure (psig) | Weight Hourly Space Velocity (gms. of succinic anhydride per gm. of catalyst per hour) | Hydrogen Flow (mole) ratio of hydrogen to succinic anhydride | Selectivity (Wt. % of gamma-butyrolactone in reaction product) | Conversion (Wt. % of succinic anhydride to gamma-butyrolactone) |
|---|---|---|---|---|---|---|---|---|---|---|---|---|
| 19 | 6.65 | 1.65 | 30 | 55 | 15 | 0 | 203 | 900 | 1.69 | 2.30 | 95.5 | 63.6 |
| 20 | 6.65 | 1.65 | 30 | 55 | 15 | 0 | 217 | 900 | 1.70 | 2.30 | 95.6 | 70.6 |
| 21 | 0 | 8.27 | 30 | 55 | 15 | 0 | 216 | 900 | 1.72 | 2.30 | 93.8 | 25.1 |
| 22 | 0 | 8.27 | 30 | 55 | 15 | 0 | 229 | 900 | 1.27 | 2.30 | 95.3 | 21.8 |
| 23 | 5.65 | 0 | 30 | 55 | 15 | 0 | 210 | 900 | 1.59 | 2.14 | 93.3 | 62.5 |
| 24 | 5.65 | 0 | 30 | 55 | 15 | 0 | 219 | 900 | 1.59 | 2.14 | 94.4 | 72.3 |
| 25 | 5.65 | 0 | 30 | 55 | 15 | 0 | 209 | 900 | 1.83 | 2.15 | 94.3 | 68.5 |
| 26 | 4.8 | 1.2 | 25 | 50 | 25 | 0 | 220 | 1500 | 0.85 | 1.97 | 94.2 | 76.9 |
| 27 | 4.8 | 1.2 | 25 | 50 | 25 | 0 | 220 | 1500 | 0.64 | 2.60 | 93.1 | 83.5 |
| 28 | 4.8 | 1.2 | 25 | 50 | 25 | 0 | 230 | 1500 | 1.19 | 3.20 | 92.1 | 88.1 |
| 29 | 4.8 | 1.2 | 18 | 50 | 25 | 7 | 230 | 1500 | 1.17 | 3.29 | 93.2 | 84.0 |
| 30 | 4.8 | 1.2 | 18 | 50 | 25 | 7 | 230 | 1500 | 1.17 | 3.30 | 94.1 | 73.1 |
| 31[1] | 5.58 | 1.4 | 18 | 50 | 25 | 7 | 230 | 1500 | 1.17 | 3.29 | 94.3 | 44.4 |
| 32[1] | 5.58 | 1.4 | 18 | 50 | 25 | 7 | 229 | 1500 | 1.17 | 3.29 | 95.4 | 38.3 |

[1]Silica gel used is Davison G-4 silica gel having a surface area of 649 m$^2$/g and a pore volume of 0.41 cc/g From Table II it can be seen that tetrahydrofuran, succinic anhydride and succinic acid were able to be recycled to the succinic anhydride hydrogenation reaction whereby such reaction products were converted to gamma-butyrolactone and the conversion rate caused to approach 100%. The presence of gamma-butyrolactone in the recycle stream increased the solubility of the succinic anhydride and succinic acid.

EXAMPLE 3

Various additional catalysts were prepared and tested for effectiveness in accordance with the procedure of Example 1 except that supports having various surface areas and porosities were utilized, namely, a silica, marketed under the trade name HiSil 210 having a surface area of 127 m$^2$/g and a pore volume of 2.58; and a molecular sieve marketed under the trade designation Silicalite (S-115) mixed with flame hydrolized alumina, Alcon C. The results of these tests are given in Table III below.

From a comparison of runs 33 and 34 of Table III with runs 28 and 29 of Table II, it can be seen that catalysts supported on HiSil 210 were less effective than the catalysts of the present invention.

EXAMPLE 4

The procedure of Example 1 was repeated except that catalysts were formed using cobalt rhenium oxide [Co(ReO$_4$)$_2$] and nickel rhenium oxide [Ni(ReO$_4$)$_2$] [the silica gel was impregnated with methanol solutions of prepared Co(ReO$_4$)$_2$ and Ni(ReO$_4$)$_2$, respectively]. The results of these tests are given in Table IV below. Two similar effectiveness tests were conducted using prior art catalysts, namely a palladium-cobalt-cobalt oxide on Ketjen silica catalyst similar to the catalyst described in U.S. Pat. No. 4,025,534 issued May 24, 1977, and a rhenium-nickel-nickel oxide on Ketjen silica catalyst similar to the catalyst described in U.S. Pat. No. 3,492,314 issued Jan. 27, 1970. The results of these tests are given in Table V.

TABLE III

Effectiveness of Nickel and Cobalt Catalysts on Various Support

| Run No. | Catalyst Wt. % Ni | Catalyst Wt. % Co | Feed Wt. % Succinic Anhydride | Feed Wt. % Tetrahydrofuran | Feed Wt. % Gamma-Butyrolactone | Temperature (°C.) | Pressure (psig) | Weight Hourly Space Velocity (gms. of succinic anhydride per gm. of catalyst per hour) | Hydrogen Flow (mole) ratio of hydrogen to succinic anhydride | Selectivity (Wt. % of gamma-butyrolactone in reaction product) | Conversion (Wt. % of succinic anhydride to gamma-butyrolactone) |
|---|---|---|---|---|---|---|---|---|---|---|---|
| 33[1] | 4.8 | 1.2 | 25 | 50 | 25 | 221 | 900 | 0.82 | 1.62 | 77.0 | 27.6 |
| 34[1] | 4.8 | 1.2 | 15 | 85 | 0 | 230 | 1500 | 0.49 | 5.25 | 45.3 | 31.3 |
| 35[2] | 1.2 | 2.4 | 25 | 50 | 25 | 211 | 900 | 0.75 | 2.65 | 86.6 | 85.5 |
| 36[2] | 1.2 | 2.4 | 25 | 50 | 25 | 214 | 900 | 0.75 | 2.65 | 80.6 | 89.2 |
| 37[2] | 1.2 | 2.4 | 25 | 50 | 25 | 217 | 900 | 0.75 | 2.65 | 71.6 | 99.2 |
| 38[2] | 1.2 | 2.4 | 25 | 50 | 25 | 220 | 1500 | 1.19 | 1.19 | 89.0 | 87.2 |

[1]HiSil 210
[2]Silicalite (S-115)

TABLE IV

Effectiveness of Nickel and Cobalt Rehenium Oxide Catalysts

| Run No. | Catalyst Wt. % Co(ReO4) | Catalyst Wt. % Ni(ReO4)2 | Feed (Wt. Succinic Anhydride in Tetra-hydrofuran) | Temperature (°C.) | Pressure (psig) | Weight Hourly Space Velocity (gms. of succinic anhydride per gm. of catalyst per hour) | Hydrogen Flow (mole ratio of hydrogen to succinic anhydride) | Selectivity (Wt. % of gamma-butyrolactone in reaction product) | Conversion (Wt. % of succinic anhydride to gamma-butyrolactone) |
|---|---|---|---|---|---|---|---|---|---|
| 39 | 3.24 | 0 | 10 | 217 | 1500 | 0.32 | 4.93 | 88.7 | 98.8 |
| 40 | 3.24 | 0 | 10 | 229 | 900 | 0.33 | 2.68 | 93.5 | 85.3 |
| 41 | 3.24 | 0 | 15 | 226 | 900 | 0.46 | 3.54 | 91.3 | 53.3 |
| 42 | 3.24 | 0 | 15 | 226 | 1500 | 0.49 | 3.36 | 93.3 | 76.0 |
| 43 | 3.24 | 0 | 10 | 215 | 1500 | 0.32 | 3.36 | 83.8 | 98.0 |
| 44 | 3.24 | 0 | 10 | 223 | 900 | 0.33 | 3.25 | 92.9 | 71.0 |
| 45 | 0 | 2.25 | 10.5 | 230 | 1500 | 0.33 | 4.50 | 87.0 | 95.4 |
| 46 | 0 | 2.25 | 15 | 228 | 1500 | 0.54 | 2.67 | 92.7 | 81.9 |
| 47 | 0 | 2.25 | 20 | 232 | 1500 | 0.39 | 2.78 | 85.5 | 95.4 |

TABLE V

Effectiveness of Prior Art Catalysts

| Run No. | Catalyst | Feed (Wt. Succinic Anhydride in Tetra-hydrofuran) | Temperature (°C.) | Pressure (psig) | Weight Hourly Space Velocity (gms. of succinic anhydride per gm. of catalyst per hour) | Hydrogen Flow (mole ratio of hydrogen to succinic anhydride) | Selectivity (Wt. % of gamma-butyrolactone in reaction product) | Conversion (Wt. % of succinic anhydride to gamma-butyrolactone) |
|---|---|---|---|---|---|---|---|---|
| 48 | Pd—Co—CoO | 60 | 215 | 1500 | 0.8 | 4 | 63.5 | 16.5 |
| 49 | Re—Ni—NiO | 10 | 257 | 900 | 0.22 | 4 | 35 | 78 |

What is claimed is:

1. A catalyst comprised of transition metals, their oxides and mixtures thereof selected from the group consisting of nickel, cobalt, nickel oxide, cobalt oxide, cobalt rhenium oxide and nickel rhenium oxide supported on silica gel having a surface area in the range of from about 50 m$^2$/g to about 500 m$^2$/g and a pore volume in the range of from about 0.25 cc/g to about 2.5 c/g, said transition metals, their oxides or mixtures thereof being present on said silica gel in an amount in the range of from about 0.1% to about 10% by weight of said catalyst and said nickel not exceeding about 4.8% by weight of said catalyst.

2. The catalyst of claim 1 wherein said transition metals, their oxides and mixtures thereof are comprised of nickel present in an amount of about 4% by weight of said catalyst.

3. A method of preparing a catalyst comprised of transition metals, their oxides and mixtures thereof selected from the group consisting of nickel, cobalt, nickel oxide, cobalt oxide, cobalt rhenium oxide and nickel rhenium oxide supported on silica gel, said silica gel having a surface area in the range of from about 50 m$^2$/g to about 500 m$^2$/g and a pore volume in the range of from about 0.25 cc/g to about 2.5 cc/g comprising the steps of:

(a) calcining said silica gel at a temperature and for a time period sufficient to remove hydroxyl groups therefrom;

(b) impregnating said calcined silica gel with an alcohol solution of transition metal salts which are thermally decomposable to said transition metals, their oxides and mixtures thereof, said transition metal salts being impregnated in said silica gel in an amount such that upon decomposition, the resulting metals and oxides formed are present on said catalyst in an amount less than about 10% by weight of said catalyst;

(c) evaporating said alcohol from the resulting impregnated silica gel in air;

(d) after step (c), heating said impregnated silica gel in an inert gas atmosphere at a temperature and for a time period sufficient to decompose said transition metal salts to said transition metals, their oxides or mixtures thereof; and (e) after step (d), heating said impregnated silica gel in a hydrogen atmosphere at a temperature in the range of from about 75° C. to about 300° C. for a time period in the range of from about 12 hours to about 24 hours to thereby activate said catalyst.

4. The method of claim 3 wherein said silica gel is calcined in accordance with step (a) at a temperature in the range of from about 300° C. to about 550° C. for a time period in the range of from about 3 hours to about 24 hours.

5. The method of claim 3 wherein silica gel is impregnated with said transition metal salts in accordance with step (b) in amounts whereby the resulting activated catalyst contains transition metals, their oxides or mixtures thereof in amounts in the range of from about 0.1% to about 10% by weight of said catalyst and the resulting impregnated silica gel is heated in accordance with step (d) over an increasing temperature range of from about 130° C. to about 550° C. and over a time period in the range of from about 3 hours to about 24 hours.

6. The method of claim 3 wherein said silica gel is impregnated in step (b) with nickel salts in amounts whereby the resulting activated catalyst contains nickel in an amount of about 6% by weight, and said silica gel is heated in accordance with step (d) over an increasing temperature range of from about 130° C. to about 550°)

C. and over a time period in the range of from about 3 to about 24 hours.

7. The method of claim 3 wherein said silica gel is impregnated with a cobalt rhenium oxide salt in an amount whereby the resulting activated catalyst contains cobalt rhenium oxide in an amount of about 2.5% by weight, and the resulting impregnated silica gel is heated in accordance with step (d) over an increasing temperature range of from about 130° C. to about 550° C. and over a time period in the range of from about 3 hours to about 24 hours.

8. The method of claim 3 wherein said silica gel is impregnated with nickel rhenium oxide salt in an amount whereby the resulting activated catalyst contains nickel rhenium oxide in an amount of about 2.5% by weight, and the resulting impregnated silica gel is heated in accordance with step (d) over an increasing temperature range of from about 130° C. to about 550° C. and over a time period in the range of from about 3 hours to about 24 hours.

9. The catalyst of claim 1 wherein said transition metals, their oxides and mixtures thereof are comprised of cobalt rhenium oxide, said cobalt rhenium oxide being present on said silica gel in an amount in the range of from about 0.5% to about 5.0% by weight of said catalyst.

10. The catalyst of claim 9 wherein said cobalt rhenium oxide is present on said silica gel in an amount of about 2.5% by weight of said catalyst.

11. The catalyst of claim 1 wherein said transition metals, their oxides and mixtures thereof are comprised of nickel rhenium oxide, said nickel rhenium oxide being present on said silica gel in an amount in the range of from about 0.5% to about 5.0% by weight of said catalyst.

12. The catalyst of claim 11 wherein said nickel rhenium oxide is present on said silica gel in an amount of about 2.5% by weight of said catalyst.

* * * * *

UNITED STATES PATENT AND TRADEMARK OFFICE
CERTIFICATE OF CORRECTION

PATENT NO. : 5,086,030

DATED : February 4, 1992

INVENTOR(S) : Geir Bjornson and Joel J. Stark

It is certified that error appears in the above-identified patent and that said Letters Patent is hereby corrected as shown below:

Col. 1, change lines 15-19 to:

--2. Description of the Prior Art
 Gamma-butyrolactone is a stable compound which has a variety of uses, not the least of which is as an intermediate in the manufacture of various other compounds, e.g., vinylpyrrolidone.--;

Col. 2, line 15, change "oxide" to --oxide,--;

Cols. 11-12, TABLE IV, line 2 (title), change "Rehenium" to --Rhenium--; and

Cols. 11-12, TABLE IV, line 11, change "$Co(ReO_4)$" to --$Co(ReO_4)_2$--.

Col. 11, claim 2, line 48, after "weight" and before "of" add --and nickel oxide present in an amount of about 2.5% by weight--.

Signed and Sealed this

Twentieth Day of April, 1993

*Attest:*

MICHAEL K. KIRK

*Attesting Officer*   *Acting Commissioner of Patents and Trademarks*